Figure 1:
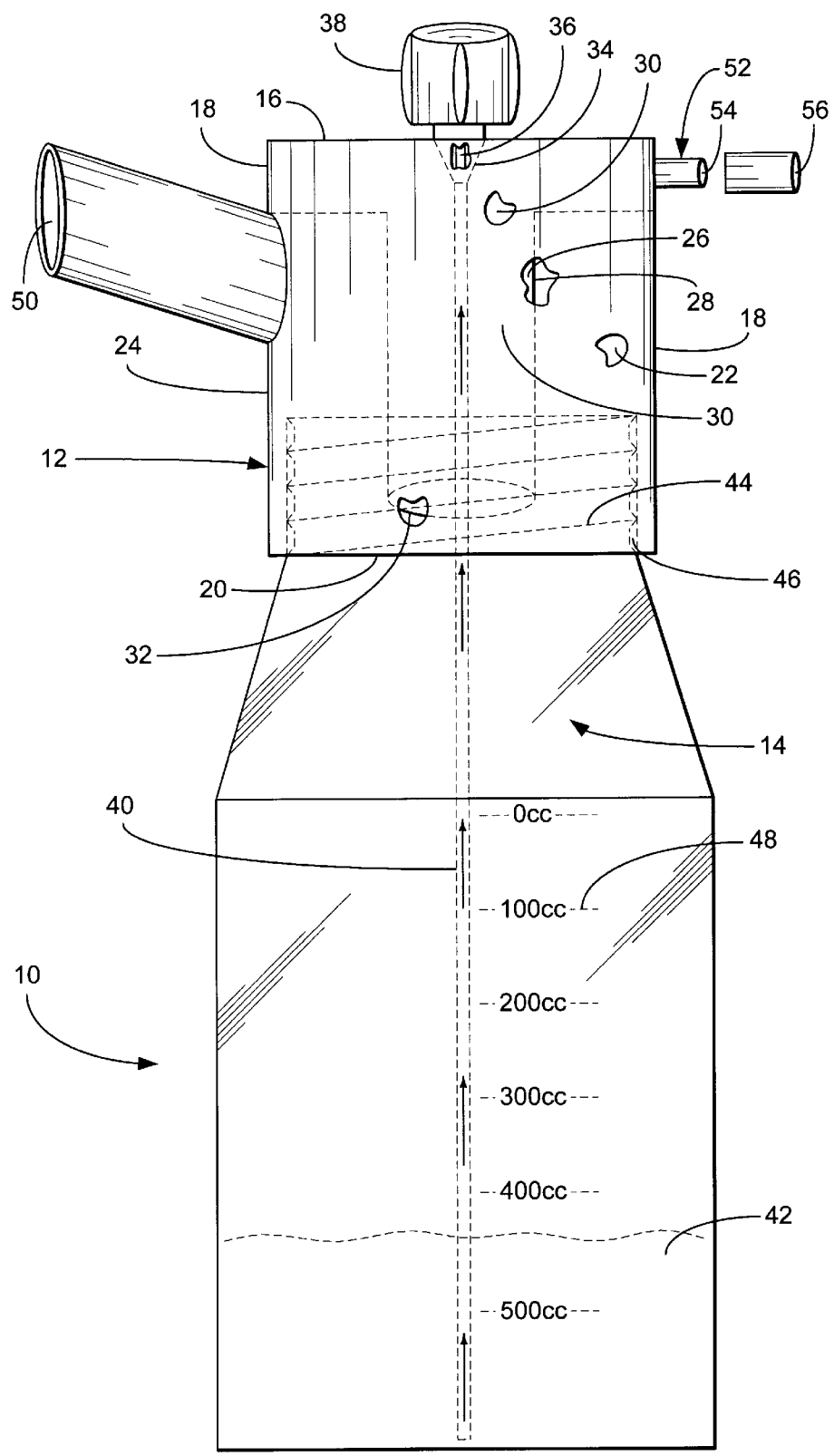

US006041776A

United States Patent [19]

Briggs, III

[11] Patent Number: 6,041,776
[45] Date of Patent: Mar. 28, 2000

[54] MEDICAL NEBULIZATION DEVICE

[76] Inventor: Stephen W. Briggs, III, P.O. Box 1503, Orangevale, Calif. 95662

[21] Appl. No.: 09/078,736

[22] Filed: May 14, 1998

[51] Int. Cl.$^7$ .................................................... A61M 16/00

[52] U.S. Cl. ............................... 128/200.21; 128/200.14; 128/203.12; 128/204.14

[58] Field of Search ......................... 128/200.21, 200.24, 128/200.11, 203.12, 204.14, 202.27, 200.14; 239/338, 352

[56] References Cited

U.S. PATENT DOCUMENTS

| | | | |
|---|---|---|---|
| 4,805,609 | 2/1989 | Roberts et al. .................... | 128/200.21 |
| 4,827,921 | 5/1989 | Rugheimer ......................... | 128/202.27 |
| 4,951,661 | 8/1990 | Sladek ................................ | 128/202.27 |
| 5,277,175 | 1/1994 | Riggs et al. ....................... | 128/203.12 |
| 5,570,682 | 11/1996 | Johnson ............................. | 128/200.16 |

*Primary Examiner*—John G. Weiss
*Assistant Examiner*—V. Srivastava
*Attorney, Agent, or Firm*—Donald E. Nist

[57] ABSTRACT

The improved medical nebulization device includes a head and a removeable depending liquid reservoir. The head has a closed top, closed sides and open bottom defining a central space in which is secured a nebulization chamber having closed sides and an open top and open bottom. A nebulization baffle is connected to the head top and extends into the nebulization chamber. A liquid draw tube is connected to the baffle and depends from the chamber into the reservoir. A nebulized aerosol output port extends between the space outside the chamber and a point peripheral of the head for supplying nebulized aerosol to a patient. An auxiliary multiple gas entrainment inlet port, with removeable cap, extends into the chamber at a point remote from the output port and is adapted to supply auxiliary gases such as a mixture of oxygen and helium. The liquid reservoir in one embodiment includes a graduated liquid measuring scale and is transparent. The baffle in one embodiment is an annular flow aerosol nozzle secured to the underside of the top of the head. The device permits accurate adjustment of the types of nebulized liquid-gas mixture supplied to a patient.

7 Claims, 2 Drawing Sheets

MEDICAL NEBULIZATION DEVICE

BACKGROUND OF THE INVENTION

1. Field of the Invention

The present invention generally relates to a medical device and more particularly to an improved medical nebulization device which provides means for supplying one or more auxiliary gases for nebulization, as well as a main stream of nebulizing gases.

2. Prior Art

Aerosol therapy in the field of respiratory care is indicated for retained secretions, humidification of inspired gas and to directly administer bronchodilator medications to the smooth muscles of a patient's airways. The administration of aerosols improves bronchial hygiene, hydrates retained secretions and, when used with bronchial dilators, relieves shortness of breath in compromised patients, that is, those with asthmatic or chronic obstructive pulmonary conditions (COPD).

Typically, asthmatic and COPD patients are treated with a conventional hand held nebulizing device to deliver aerosolized medications to the sensitized airways. For example, in the conventional emergency treatment of asthma, a hand held small volume nebulizer is utilized with a typical dose of 0.5 cc of Albuterol Sulfate solution, repeated 3–4 times in an E.R. in combination with steroids to help reduce the inflammatory process and shortness of breath in the patient.

Moreover, it has been found that the early administration of large doses (10–15 mg) per hour of medication/saline by means of a nebulizer can have positive dramatic effects on patient outcomes, reducing hospital stay times by as much as 3 days. The nebulizer not only delivers large amounts of medication to the affected areas but deposits them even in the smaller peripheral airways. Large amounts of nebulized saline delivered by the nebulzier assist in breaking down mucus plugs in the patient's airways and cooling and moisturizing those airways.

For those compromised asthmatic and COPD patients who exhibit swollen and mucus obstructed airways, it may also be beneficial to utilize a secondary and lighter weight inert gas to deliver medications to bypass obstructed airways. Helium, an inert and metabolically stable gas, readily diffuses into swollen airways. A mixture of 80% oxygen and 20% helium would therefore be useful for such purposes.

The ideal nebulizing device for medical use would permit continuous nebulization for extended periods of time, utilizing small particle size aerosol for maximum deposition in the airways, and also have the capability of introducing in a controlled manner through a secondary inlet port lighter gas as needed to facilitate deposition of aerosolized medication into the lung parenchyma. Such device should be driven by a primary gas source of either oxygen or air but permit bleeding in of lighter gas as required for a special application.

Currently, the continuous nebulizing devices available do not meet the requirements set forth above for the ideal device. None of the current devices are capable of entraining a secondary small amount of special inert gas from a supplemental gas source. It would be highly desireable to provide a medical nebulizing device meeting the criteria for the ideal device.

SUMMARY OF THE PRESENT INVENTION

The improved nebulizing device of the present invention satisfies all the foregoing needs. The device is substantially as set forth in the Abstract of the Disclosure.

Thus, the device comprises a nebulizing head and a removeable liquid medication-holding reservoir attached to the bottom thereof. The head has a closed top, closed sides and open bottom defining a central space in which is secured a nebulization chamber having closed sides and an open top and bottom. The chamber can be funnel or hour glass shaped or the like.

A nebulization baffle or annular flow aerosol nozzle is secured to the underside of the head top and disposed within the chamber. A liquid syphon or draw tube has its upper end connected to the baffle and extends down through the chamber and into the reservoir.

A nebulized aerosol output port extends between the space outside the chamber in the head and a point peripheral of one side of the head and may have an extension which directs the aerosol towards and into the patient.

Of primary importance, an auxiliary multiple gas entrainment inlet port is provided which, at its outer end has a removeable seal cap, and extends from a point peripheral of the head and remote from the outlet port to a point within the chamber. This inlet port permits auxiliary gases such as light weight helium or another gas alone or in admixture with oxygen or air or the like to be bled into the primary gas stream flow path through the nebulizer head and thus to exit with and as part of the output aerosol when and as needed, without interrupting the continuous output flow of aerosol from the device. Such primary flow powers the auxiliary gas through the device.

Preferably, the primary oxygen and/or air flow through the device is driven by pressurized gas from a flowmeter. The gas passing through the device draws liquid such as a mixture of medication and saline solution from the reservoir up the draw tube by a Venturi effect to and through a spraying and baffle system within the device to provide a fine aerosol mist of, for example, 2.5–3.0 um particle size. The device may be driven by a primary gas source of, for example, 50 psi operating at, for example, 13 liters/min. to provide about 25–30 cc/hr of aerosol.

Preferably, the reservoir has a graduated scale on it and a large capacity of, for example, about 200–500cc or more of medication/saline solution so that continuous nebulization can be carried out for up to about 20 hrs or more without recharging the reservoir.

Further features of the improved nebulization device of the present invention are set forth in the following detailed description and accompanying drawings.

DRAWINGS OF THE INVENTION EMBODIMENTS

FIG. 1 is a schematic side elevation, partly in dotted outline and partly broken away, showing a first preferred embodiment of the improved nebulization device of the present invention; and, FIG. 2 is a schematic side elevation, partly broken away and partly in cross-section, of a second preferred embodiment of the improved nebulization device of the present invention, showing a mixture of medication and saline solution in the reservoir of the device, and with the reservoir separated from the device head.

DETAILED DESCRIPTION OF THE EMBODIMENTS

FIG. 1

Now referring more particularly to FIG. 1 of the drawings, a first preferred embodiment of the improved nebulizing device of the present invention is schematically depicted therein.

Thus, device 10 is shown which comprises a nebulizing head 12 releasably connected to a liquid-containing reservoir 14. Head 12 includes a closed top 16, closed sides 18 and an open bottom 20 collectively defining a generally central space 22. Head 12 is preferably in the form of a shell 24 of glass, plastic or the like, and is preferably generally cylindrical.

A nebulization chamber 26 is secured at its upper end to the inner surfaces of sides 18 and depends therefrom within the central portion of space 22 below top 16 and above bottom 20 and may be formed as an integral part of shell 24, if desired.

In FIG. 1, chamber 26 is shown as having closed sides 28 and open top 30 and open bottom 32, and is generally funnel shaped.

Head 12 also includes a nebulization baffle 34 of conventional design secured to the underside of head top 16 and having a central passageway 36 extending vertically down through top 16, through which the main stream of nebulizing gas (not shown) can pass into and through baffle 34 after connection of a primary gas line (not shown) to baffle 34 through a nipple nut adapter 38 carried by top 16. The bottom of baffle 34 is connected to the upper end of a hollow draw tube 40 up through which liquid 42 in reservoir 14 is drawn by suction or Venturi effect into baffle 34 for aerosolizing, that is, nebulizing.

Head 12 is relasably secured to reservoir 14 by mating threads 44 and 46, respectively, in the inner surface of the bottom portion of head 12 and outer surface of reservoir 14 at the upper end thereof. Preferably, reservoir 14 is transparent and bears a graduated vertical scale 48 for determining the amount of liquid 42 in reservoir 14. Scale 48 can be molded into or separately applied to reservoir 14, as desired.

Head 12 also includes a nebulized aerosol output port 50 defined in a side 18 of head 12 and extending into communication with space 22 but external of chamber 26, as shown in FIG. 1. Port 50 extends peripheraly of head 12 and preferably is elongated and funnel shaped for delivery of the nebulized aerosol to a patient.

Head 12 further includes a novel auxiliary gas entrainment inlet port 52 defined in a side 18 and extending into space 22, specifically into the upper portion of chamber 26. Inlet port 52 is provided with an external tube portion 54 extending peripherally of shell 24, and a removeable seal cap 56, in FIG. 1 shown removed from portion 54. The auxiliary gas can be a light weight gas such as helium or the like, fed alone through inlet port 52 to chamber 26, or a mixture of such gas with oxygen and/or air or the like.

This auxiliary gas is used intermittently as needed and is powered through device 10 by primary gas such as oxygen and/or air driven under pressure into device 10 from a pressurized gas supply source. Such source is connected to device 10 through nipple 38 and the primary gas passes through passageway 36 in baffle 34 and then into nebulization chamber 26, causing by venturi effect liquid 42 to be drawn up through tube 40 into baffle 34 for nebulization with such primary gas.

The resulting aerosol exits chamber 26 and out of device 10 through output port 50 to the patient. The auxiliary gas from inlet port 52 meets the nebulized aerosol in chamber 26 and exits therewith through port 50. In effect, such auxiliary gas is bled into the flowstream in head 12 when and as needed, without interrupting the production of aerosol and its output from device 10.

Device 10 can therefore be operated to provide an intermittent or continuous output of nebulized aerosol, preferably a continuous stream of the aerosol. Usually, the auxiliary gas or gases are used for periodic bleeding into the main gas flow in device 10 for specialized augmentation of the content of the aerosol output. Device 10 thus provides features which improve the function of a medical nebulizer for improved treatment of a patient, in contrast to conventional medical nebulizers.

FIG. 2

Figure 2:
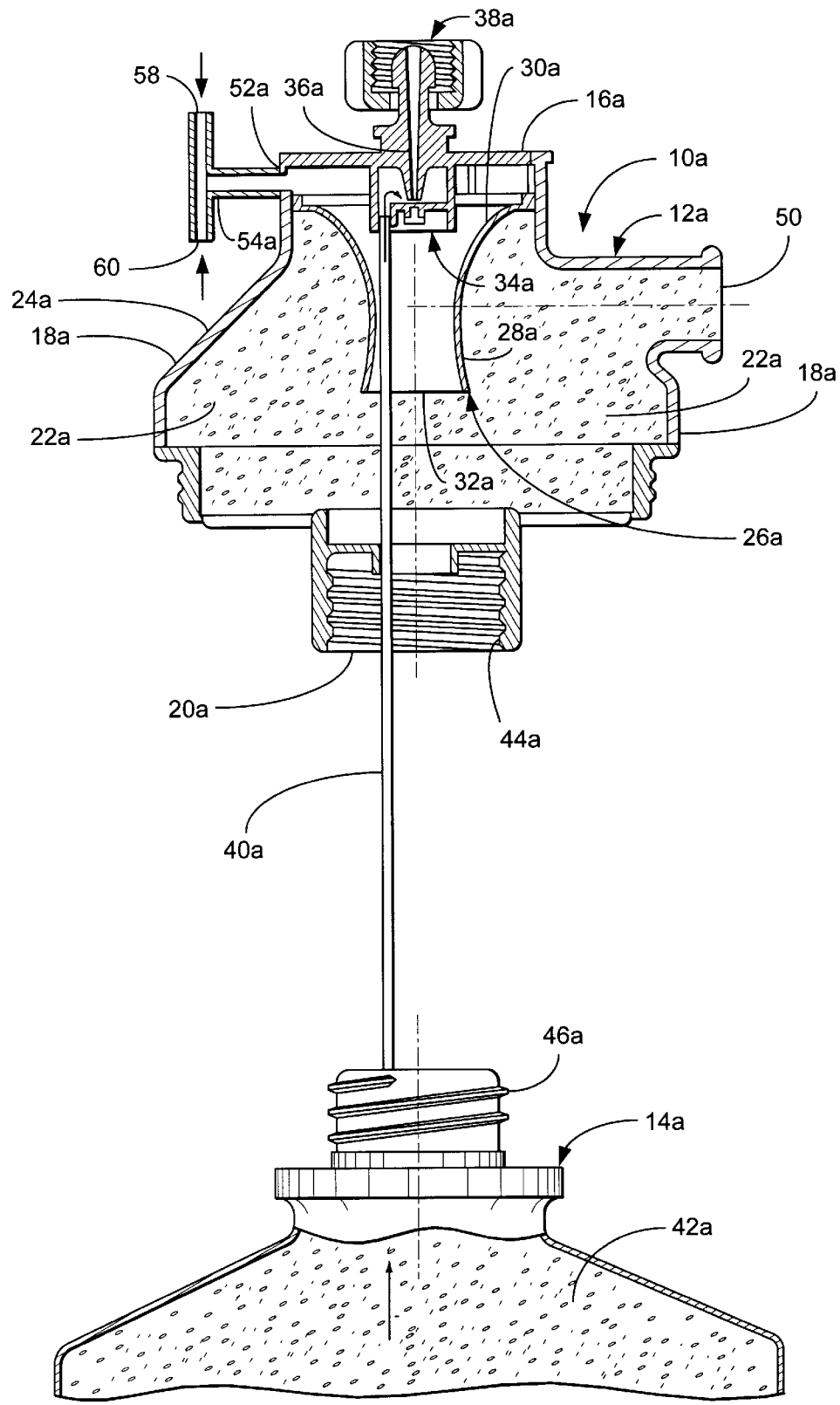

A second preferred embodiment of the improved medical nebulization device of the present invention is schematically depicted in FIG. 2. Thus, device 10a is shown. Components thereof similar to those of device 10 bear the same numerals but are succeeded by the letter "a".

Device 10a is substantially identical to device 10 except as follows:

a) The detailed configuration of the annular flow aerosol nozzle 34a comparable to the baffle of FIG. 1 is shown, liquid 42a being drawn up through tube 40a into the bottom portion of nozzle 34a to a point immediately below the lower end of passageway 36a;

b) Sides 28a of nebulization chamber 26a are hour-glass shaped with a wider upper end and flared lower end for improved secondary throat entrainment of aerosol particles, in contrast to the vertical tubular sides 28 of chamber 26; and, c) Auxiliary gas inlet port 52a has a tubular portion 54a which extends peripheral of shell 24a and is bifurcated into two separate injection lines 58 and 60 for separate introduction of two different gases from separate pressurized sources.

The other features and advantages of device 10a are similar to those of device 10. Accordingly, devices 10 and 10a have substantial advantages over the prior art devices.

Various modifications, changes, alterations and additions can be made in the improved medical nebulization device of the present invention, its components and parameters. All such modifications, changes, alterations and additions as are within the scope of the appended claims form part of the present invention.

What is claimed is:

1. An improved medical nebulization device, said device comprising, in combination:

a) a nebulizer head comprising, in combination:
   i) a shell having a closed top and sides and open bottom defining a generally central space;
   ii) a nebulization chamber having an open top and bottom and closed sides secured at said nebulization chamber sides to said shell sides within said shell central space, said nebulization chamber sides being curved downwardly and inwardly to form a secondary entrainment throat;
   iii) an annular flow aerosol nozzle secured to the underside of said shell top within said nebulization chamber;
   iv) an oxygen supply inlet extending through said shell top into said nozzle;
   v) a liquid draw tube connected to said nozzle and depending extending downwardly therefrom;
   vi) a nebulized aerosol output port defined in one of said shell sides peripheral of said nebulization chamber; and,
   vii) an auxiliary multiple gas entrainment inlet port having a removable cap, said auxiliary inlet port being defined in another of said shell sides and extending into the upper portion of said nebulization chamber; the bottom of said head having means for releasably connecting said head to a liquid reservoir; and, b) a liquid reservoir extending below and releasably connected to said head through said connector means, said liquid draw tube extending into said reservoir, said reservoir including a closed bottom and sides and open top sealed by said connector means to said head.

2. The improved nebulization device of claim 1 wherein said shell top includes adapter means for releasably connecting said head to a source of oxygen.

3. The improved nebulization device of claim 2 wherein said auxiliary multiple gas entrainment inlet port has a plurality of separate spaced injection lines, each one of which lines has a removable cap.

4. The improved nebulization device of claim 3 wherein said nebulized aerosol output port extends peripheral of said shell and forms a funnel for directing said nebulized aerosol to a patient.

5. The improved nebulization device of claim 4 wherein said auxiliary multiple gas entrainment inlet port extends into said shell peripheral of said annular flow aerosol nozzle.

6. The improved nebulization device of claim 5 wherein said liquid draw tube extends into the bottom of said annular flow aerosol nozzle and wherein said nebulization chamber is curved downwardly in an hour-glass shape to form said secondary entrainment throat.

7. The improved nebulization device of claim 6 wherein said device comprises at least one of glass and clear plastic and wherein auxiliary multiple gas entrainment inlet port is adapted to be connected to sources of oxygen and helium.

* * * * *